United States Patent
Greenland et al.

(10) Patent No.: US 6,599,514 B1
(45) Date of Patent: Jul. 29, 2003

(54) ANTIFUNGAL COMPOSITION

(75) Inventors: Andrew James Greenland, Bracknell (GB); Angel Manuel Fuentes Mateos, Bracknell (GB)

(73) Assignee: Syngenta Limited, Guildford Surrey (GB)

(*) Notice: Subject to any disclaimer, the term of this patent is extended or adjusted under 35 U.S.C. 154(b) by 0 days.

(21) Appl. No.: 09/446,472

(22) PCT Filed: Jul. 9, 1998

(86) PCT No.: PCT/GB98/02010
§ 371 (c)(1), (2), (4) Date: Dec. 21, 1999

(87) PCT Pub. No.: WO99/02038
PCT Pub. Date: Jan. 21, 1999

(30) Foreign Application Priority Data

Jul. 10, 1997 (GB) .............................. 9714564

(51) Int. Cl.$^7$ .................. A01N 25/34; A61K 35/78; C12P 21/06; C07K 1/100
(52) U.S. Cl. .................. 424/404; 424/439; 424/755; 424/776; 424/725; 435/69.1; 530/350; 530/370
(58) Field of Search .................. 424/195.1, 725, 424/439, 757, 754, 776, 755; 530/350, 370; 514/339, 642, 643; 435/69.1

(56) References Cited

U.S. PATENT DOCUMENTS

| | | | |
|---|---|---|---|
| 4,303,668 A | * | 12/1981 | Hasegawa et al. |
| 4,361,588 A | | 11/1982 | Herz |
| 5,705,152 A | * | 1/1998 | Plummer |
| 5,750,504 A | * | 5/1998 | Broekaert et al. |
| 5,773,694 A | | 6/1998 | Broekaert et al. |
| 6,001,864 A | * | 12/1999 | Akashi et al. |

FOREIGN PATENT DOCUMENTS

| | | | |
|---|---|---|---|
| EP | 0 440 304 A1 | | 8/1991 |
| EP | 0513922 A1 | | 12/1992 |
| FR | 2 663 198 | | 12/1991 |
| JP | 02076809 | * | 3/1990 |
| JP | 03081211 A | | 4/1991 |
| WO | WO 91/18984 | | 12/1991 |
| WO | WO 92/15691 | | 2/1992 |
| WO | WO 92/21699 | | 12/1992 |
| WO | WO 93/04586 | | 3/1993 |
| WO | WO 93/05153 | | 3/1993 |
| WO | WO 94/08009 | | 4/1994 |
| WO | WO 94/11511 | | 5/1994 |
| WO | WO 95/04754 | | 2/1995 |
| WO | WO 95/05467 | | 2/1995 |
| WO | WO 95/18229 | | 7/1995 |
| WO | WO 95/18859 | | 7/1995 |
| WO | WO 95/24486 | | 9/1995 |
| WO | WO 96/40121 | * | 12/1996 |
| WO | WO 97/03674 | * | 2/1997 |
| WO | WO 97/21814 | | 6/1997 |
| WO | WO 97/21815 | | 6/1997 |

OTHER PUBLICATIONS

Tailor et al., J of Biology Chemistry (1997), 272(390: 24480–24487. a novel family of small cysteine antimicrobial peptides from seeds of Impatiens balsamina is derived from a single precursor protein.*
Frazier et al., Food Microbiology (1978), McGraw–Hill, Inc., USA, pp. 17–45 and 154–170.*
Frazier et al., Food Microbiology, pp. 17–45 and 154–170. McGraw–Hill, Inc., 1978.*
Tailor et al., J of Biology Chemistry, 272(39): 24480–24487. A novel family of small–cysteine–rich antimicrobial peptides from seed of Impatiens balsamina is derived from a single precursor protein, 1997.*
Hawley, The Condensed Chemical Dictionary, 8th edition, Litton Educational Publishing, Inc., pp. 346,840, 907 and 937, 1971.*
Colby, S.R., Weeds, vol. 15, pp. 20–22, 1967.
Waterman, M.S. et al., J. Mol. Biol., vol. 197, pp., 723–728, 1987.
Broekaert, W.F. et al., FEMS Microbiology Letters, vol. 69, pp. 55–60, 1990.
Cammue, B.P.A. et al., J. of Biol. Chemistry, vol. 267, No. 4, pp. 2228–2233, Feb. 5, 1992.
Terras, F.R.G., et al., J. of Biol. Chemistry, vol. 267, No. 22, pp. 15301–15309, Aug. 5, 1992.
Broekaert, W.F., et al., Biochemistry, vol. 31, pp. 4308–4314, 1992.
Sela–Buurlage, M.B., et al., Plant Physiol., vol. 101, pp. 857–863, 1993.
Myers, E.W., et al., CABIOS, vol. 4, No. 1, pp. 11–17, 1988.
Wilbur, W.J., et al., PNAS, vol. 80. pp. 726–730, Feb. 1983.
Parish, M.E., et al., "Methods for Evaluation", in Antimicrobials in Food, Davidson, P.M. and Branen, A.L., eds, Marcel Dekker, Inc., New York, New York, 1993, pp. 597–615.

* cited by examiner

Primary Examiner—Christopher R. Tate
Assistant Examiner—Michele C. Flood
(74) Attorney, Agent, or Firm—Hale & Dorr LLP

(57) ABSTRACT

Antifungal compositions having enhanced antifungal activity comprising an antifungal agent and a food additive are described. Also described are a method for inhibiting fungal growth using the compositions with enhanced activity and the use of a food additive to enhance the antifungal properties of an antifungal agent.

12 Claims, 4 Drawing Sheets

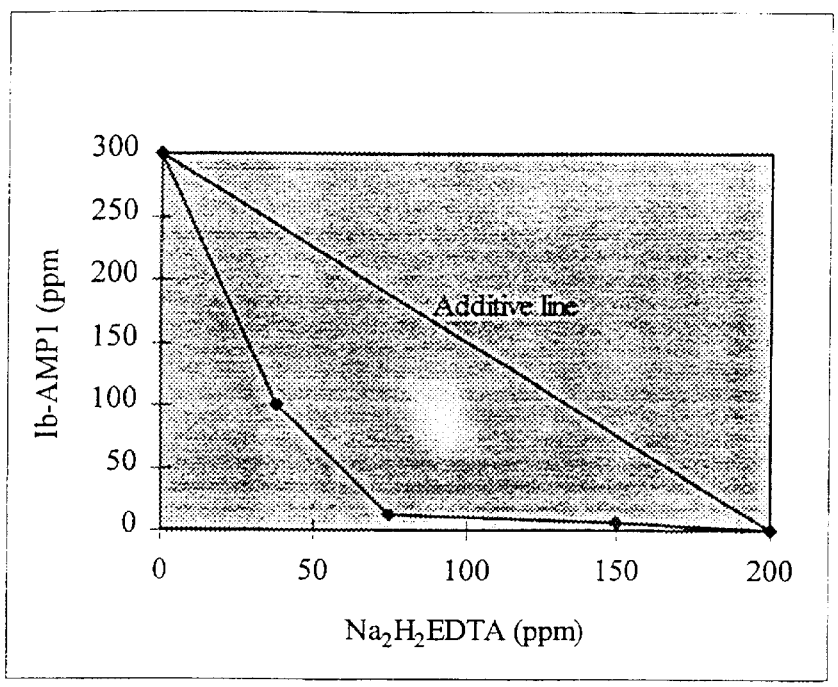
Fig. 1. Isobologram of the combination of Ib-AMP1 with Na$_2$H$_2$EDTA against *P. chrysogenum*.
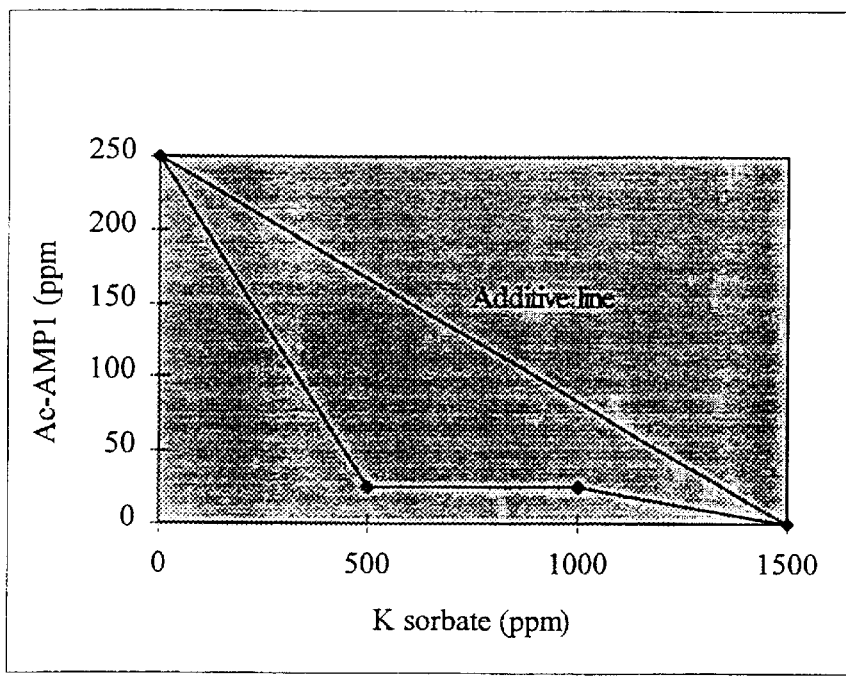
Fig. 2. Isobologram of the combination of Ac-AMP1 with K sorbate against *P. roquefortii*.

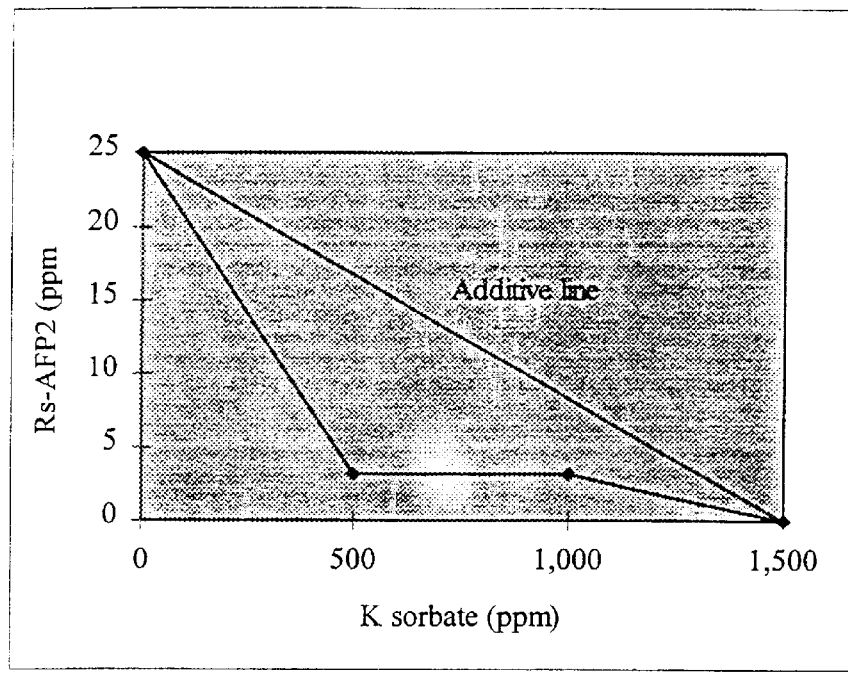
Fig. 3. Isobologram of the combination of Rs-AFP2 with K sorbate against *P. roquefortii*.
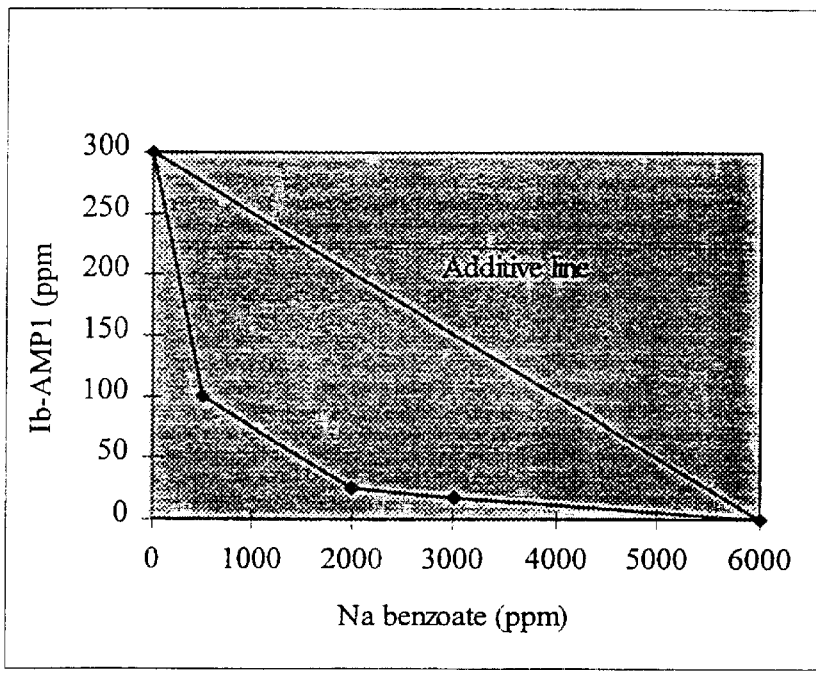
Fig. 4. Isobologram of the combination of Ib-AMP1 with Na benzoate against *P. chrysogenum*.

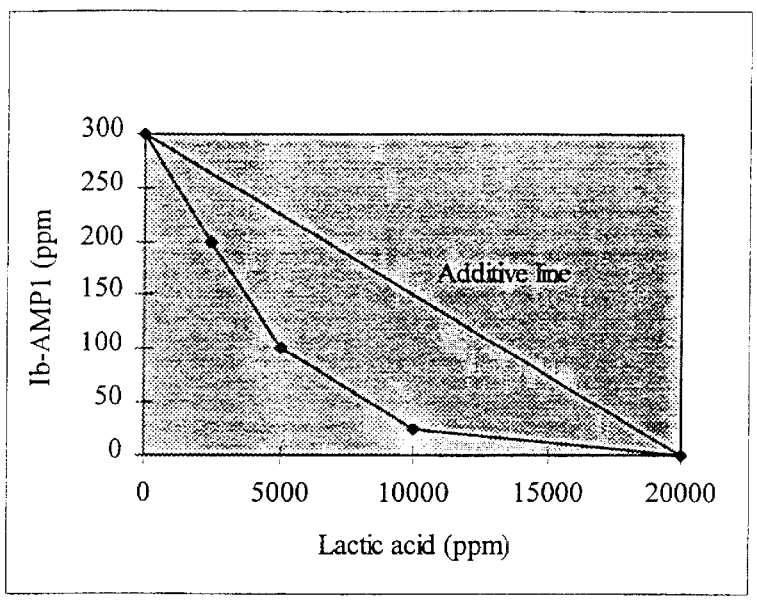
Fig. 5. Isobologram of the combination of Ib-AMP1 with lactic acid against *P. chrysogenum*.
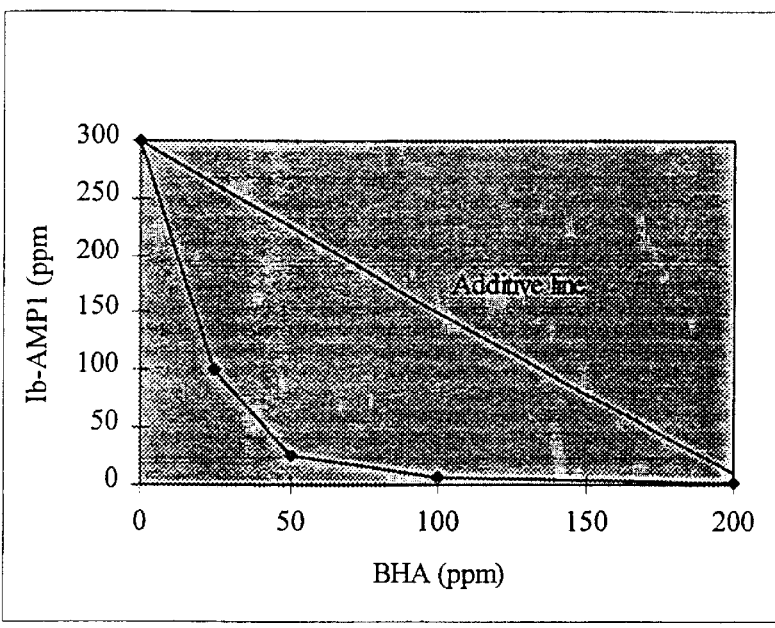
Fig. 6. Isobologram of the combination of Ib-AMP1 with BHA against *P. chrysogenum*.

Rs-AFP1
QKLCERPSGTWSGVCGNNNACKNQCINLEKARHGSCNYVFPAHKCICYFPC
Rs-AFP2
QKLCQRPSGTWSGVCGNNNACKNQCIRLEKARHGSCNYVFPAHKCICYFPC
Dm-AMP1
ELCEKASKTWSGNCGNTGHCDNQCKSWEGAAHGACHVRNGKHMCFCYFNC
Dm-AMP2 EVCEKASKTWSGNCGNTGHC
Hs-AFP1
DGVKLCDVPSGTWSGHCGSSSKCSQQCKDREHFAYGGACHYQFPSVKCFCKRQC
Ah-AMP1
LCNERPSQTWSGNCGNTAHCDKQCQDWEKASHGACHKRENHWKCFCYFNC
Ct-AMP1
NLCERASLTWTGNCGNTGHCDTQCRNWESAKHGACHKRGNWKCFCYFDC
Bn-AFP1 QKLCERPSGTWSGVCGNNNACKNQCINLEK
Bn-AFP2 QKLCERPSGTWSGVCGNNNACKN
Br-AFP1 (Q)KLCERPSGTWSGVCGNNNACKNQCIN
Br-AFP2 (Q)KLCERPSGTxSGVCGNNNACKNQCIR
Sa-AFP2 (Q)KLCQRPSGTWSGVCGNNNACRNQCI
Sa-AFP1 QKLCERPSGTWSGVCGNNNACKNQC
Sa-AFP2 QKLCQRPSGTWSGVCGNNNACRNQCI
Cb-AMP1
ELCEKASKTWSGNCGNTKHCDDQCKSWEGAAHGACHVRNGKHMCFCYFNC
Cb-AMP2
ELCEKASKTWSGNCGNTKHCDNQCKSWEGAAHGACHVRSGKHMCFCYFNC
Ca-AMP1 QEQCGNQAGGRACANRLCCSQYGYCGSTRAYCGVGCQSNCGR
Bm-AMP1 CSSHNPCPRHQCCSKYGYCGLGNDYCGLGCRGGPCDR
            H                  S
Ace-AMP1
QNICPRVNRIVTPCAVYGLGRAPIAPCCRALNDLRFVNTRNLRRAACRCLVGVVNRN
PGLRRNPRFQNIPRDCRNTFVRPFWWRPRIECGRIN
Ac-AMP1 VGECVRGRCPSGMCCSQFGYCGKGPKYCG
Ac-AMP2 VGECVRGRCPSGMCCSQFGYCGKGPKYCGR
Mj-AMP1 QCIGNGGRCNENVGPPYCCSGFCLRQPGQGYGYCKNR
Mj-AMP2 CIGNGGRCNENVGPPYCCSGFCLRQPNQGYGVCRNR
Ib-AMP1 QWGRRCCGWGPGRRYCVRWC
Ib-AMP2 QYGRRCCNWGPGRRYCKRWC
Ib-AMP3 QYRHRCCAWGPGRKYCKRWC
Ib-AMP4 QWGRRCCGWGPGRRYCRRWC

..where (Q) is assumed because of blocked N-terminus, x is non-common aminoacid (ie unassignable).

FIGURE 7

ANTIFUNGAL COMPOSITION

TECHNICAL FIELD

The present invention relates to a composition showing enhanced antifungal activity comprising one or more antifungal agents and one or more food additives, to the use of food additives to enhance the antifungal properties of an antifungal agent and to a method of inhibiting fungal growth using a composition according to the invention.

BACKGROUND OF THE INVENTION

Contamination in foodstuffs due to the presence of common food spoilage organisms is a recurring problem in the food industry. Most surprisingly we have observed an enhancement of antifungal activity when antifungal agents are combined with commonly used food additives. Furthermore, where the food additive shows antifungal activity we have observed an enhanced effect whereby the antifungal activity of the mixture is greater than would be expected. This enhancement or synergistic effect makes it possible to use a reduced amount of antifungal compound and/or food additive present in a foodstuff. This is particularly advantageous since it is highly desirable to minimise the amount of any additive present in foodstuffs both for human and animal consumption.

SUMMARY OF THE INVENTION

Accordingly in a first aspect the invention provides an antifungal composition comprising one or more antifungal agents and one or more food additives with the proviso that said composition does not contain nisin, lactoferrin and derivatives thereof, trichorzianine or lysozyme; the relative amounts of the antifungal agent(s) and the food additive(s) being such as to enhance the overall antifungal activity of the composition.

The food additive may also exhibit some antimicrobial activity especially antifungal activity when used in isolation as is observed, for example with food preservatives, and in this case the combination of the antifungal agent and the food additive will result in a synergistic effect where the antifongal activity of the mixture will be greater than that observed for each in isolation and compared to the sum of the individual results. It will be readily apparent to the man skilled in the art that in this case the antifumgal agent and the food additive present in the composition are not the same i.e. are different. The invention therefore extends to an antifungal composition comprising one or more antifungal agents and one or more food additives; the relative amounts of the antifungal agent(s) and the food additive(s) being such as to produce a synergistic effect. The invention further extends to the use of the synergistic composition in the methods of the invention hereinafter described further herein.

In a preferred embodiment the invention provides an antifungal composition comprising one or more antifungal agents and one or more food additives wherein one or more of said food additive(s) shows antimicrobial activity with the proviso that said composition does not contain nisin, lysozyme, or lactoferrin and derivatives thereof; the relative: amounts of the antifungal agent(s) and the food additive(s) being such as to produce a synergistic effect on the overall antifungal activity of the composition.

In a further preferred embodiment the invention provides a composition comprising one or more antifungal agents and one or more food additives selected from the group consisting of metal chelating agents, wetting agents, adjuvants, antioxidants, colourants, emulsifiers, stabilisers, surfactants, bleaching agents, pH control agents, flavours and flavour enhancers, sequestrants or food preservatives with the proviso that said composition does not contain nisin, lactoferrin and derivatives thereof, trichorzianine or lysozyme; the relative amounts of the antifungal agent and the food additive being such as to enhance the overall antifungal activity of the composition.

In a further aspect the invention provides the use of a food additive to enhance the antifungal properties of an antifungal agent.

As used herein the term enhance is used to denote an improvement in antifungal activity and this may be evidenced by, for example, an observed reduction in the concentration of antifungal agent required to give strong fungal growth inhibition e.g. more than 90% fungal growth inhibition. As used herein the term synergistic is used to denote an improvement in antifungal activity which can be demonstrated to be synergistic for example by application of the Colby Formula (Colby S. R. (1967) Weeds 15, 20–22) or in graphical representation in isobolograms as described by Parrish and Davidson (1993) (In: Antimicrobials in foods. Ed. By P. M. Davidson and A. L. Branen. Marcel Dekker, Inc. New York Examples of food additives include the following commonly used food additives: sorbic acid and sorbates (E200–E203), benzoic acid and benzoates (E210–E213), hydroxy-benzoates (E214–E219), sulphur dioxide and sulphites (E220–E228), biphenyl and derivatives (E230–E232), nitrites (E249–E250), nitrates (E251–E252), lactic acid (E270), lactates (E325–E327), citric acid and citrates (E330–E333), tartaric acid and tartrates (E334–E337), orthophosphoric acid and orthophosphates (E338–E341), malates (E350–E352), adipic acid (E355), succinic acid (E363), 1,4-heptonolactone (E370), nicotinic acid (E375), triammoniun citrate (E380), ammonium ferric citrate (E381), calcium disodium EDTA (E385), glycerol (E422), di-, tri- andpolyphosphates (E450a, E450b, E450c), fatty acids (E470), mono- and diglycerides of fatty acids (E471), esters of mono- and diglycerides of fatty acids (E472a-E472f), carbonates (E500, E501, E503, E504), gluconates (E576–E578), chlorine (E925), sodium hexametaphosphate, butylated hydroxyanisole (BHA) (E320), butylated hydroxytoluene (BHT)(E321), t-butyl hydroquinone (THBQ), propyl gallate, calcium heptonate, calcium phytate, diethyl ether, EDTA, disodium dihydrogen EDTA, ethyl acetate, glycerol mono-, di- and triacetates, glycine, oxystearin, propan-1,2-diol and propan-2-ol and sodium heptonate.

Particularly preferred food additives include sorbic acid and sorbates (E200–E203), benzoic acid and benzoates (E210–E213), hydroxy-benzoates (E214–E219), acetic acid and acetates (E260–E263), lactic acid (E270), lactates (E325–E327), citric acid and citrates (E330–E333), tartaric acid and tarttates (E334–E337), orthophosphoric acid and orthophosphates (E338–E341), malates (E350–E352), adipic acid (E355), succinic acid (E363), nicotinic acid (E375), calcium disodium EDTA (E385), fatty acids (E470), mono- and diglycerides of fatty acids (E471), esters of mono- and diglycerides of fatty acids (E472a-E472f), EDTA, disodium dihydrogen EDTA, ethyl acetate, glycerol mono-, di- and triacetates.

Further preferred additives include butylated hydroxy anisole, butylated hydroxytoluene and tertiary butyl hydroquinone.

We have found that when antifungal agents are used in the presence of calcium ions a significant reduction in the activity of the antiflngal agent is observed. This observation could restrict the usefulness of the technology in foods rich in calcium such as dairy products. We have now found that the problem associated with high calcium levels may be overcome by the use of chelating agents in association with the antifungal agent and most surprisingly that the presence of the chelating agent enhances the activity of the antifungal agent. Furthermore, we have found that it is possible to achieve this with levels of chelating agents, especially EDTA and salts thereof which are substantially lower than that recommended in the literature to obtain effective chelation.

Examples of particularly preferred food additives are metal chelating agents such as EDTA and its use as the disodium or calcium disodium salts; solvents and wetting agents such as organic acids e. g. lactic acid; adjuvants; and food preservatives including membrane permeabilising agents such as, for example, sorbic acid and its use as the calcium, sodium or potassium salts, benzoic acid and its use as the sodium potassium or calcium salts, antioxidants such as propyl gallate and C1–6 alkyl ethers such as butylated hydroxy anisole, butylated hydroxytoluene and tertiary butyl hydroquinone.

The use of acids and salt or ester derivatives thereof or C1–6 alkyl ethers as food additives is most particularly preferred.

Further examples of food additives may be found in 'Handbook of Food Additives', edited by Michael and Irene Ash, Gower (1995).

Antifungal agents which are particularly preferred for use in the composition, methods and uses according to the invention are those which are obtainable from natural sources. It is also preferred that the antifungal agents are heat stable and preferably also stable to proteolytic degradation. Such stability is particularly advantageous since foodstuffs are often subjected to very high temperatures during preparation, processing and packaging. The antifungal composition of the invention therefore preferably comprises one or more heat stable antifungal agents.

As used herein the term heat stable is used to denote retention of antifungal activity after incubation at 85° C. for 20 minutes or at 90° C. for 10 minutes and the term stable to proteolytic degradation is used to denote lack of susceptibility to digestion by common proteases such as trypsin.

It is further preferred that the antifungal agents exert their activity by affecting fungal cell membranes such as by acting as membrane perturbing agents. In a particularly preferred combination the antifungal agent is a membrane perturbing agent which is heat stable and stable to proteolytic degradation.

In a further aspect the invention provides an antifungal composition comprising one or more antifungal agents wherein one or more of said antifungal agents is derived from a plant or seed derivative thereof and one or more food additives wherein at least one of said food additives is an acid or salt or ester derivative thereof or a C1–6 alkyl ether, the relative amounts of the antifungal agent(s) and the food additive(s) being such as to enhance the overall antifungal activity of the composition.

In a preferred embodiment of the above aspect of the invention we provide an antifungal composition wherein one or more of said food additive(s) shows antiflingal activity; the relative amounts of the antifungal agent(s) and the food additive(s) being such as to produce a synergistic effect on the overall antifungal activity of the composition.

In the above aspect the food additive is preferably selected from the group EDTA, sorbic acid, lacticacid, benzoic acid or a salt or ester derivative thereof, propyl gallate, butylated hydroxy anisole, butylated hydroxytoluene or tertiary butyl hydroquinone.

The antifungal agent is preferably derived from plants or seeds derived therefrom belonging to plant families such as Brassicaceae also known as Cruciferae, Compositae, Leguminosae; Amaranthaceae, Hiprocastanaceae, Saxifragaceae, Gramineae and Alliaceae and more preferably from the following genuses: Raphanus, Heuchera, Aesculus, Clitoria, Brassica, Briza, Sinapsis, Cnicus, Allium, Amaranthus, Impatiens, Mirabilis and Capsicum., most preferably from Raphanus, e. g. *Raphanus sativus*; Sinapsis, e. g. *Sinapsis alba*; Amaranthus, e. g. *Amaranthus caudatus*; Impatiens, e. g. *Impatiens balsamina*; Mirabilis, e. g. *Mirabilis japa*; Brassica e. g. *Brassica napus*.

Examples of antifungal agents which are particularly preferred for use in the compositions, methods and uses according to the invention include those capable of being isolated from natural sources such as plants and the seeds thereof, such as for example the antifungal proteins described in Published International Patent Application Nos W092115691, W092/21699, W093/05153, W093/04586, W094/11511, W095/04754, W095/18229, W095/24486, W097/21814 and W097/21815 including Rs-AFPI, Rs-AFP2, Dm-AMP1, Dm-AMP2, Hs-AFP1, Ah-AMP1, Ct-AMP1, Ct-AMP2, Bn-AFP1, Bn-AFP2, Br-AFP1, Br-AFP2, Sa-AFP1, Sa-AFP2, Cb-AMP1, Cb-AMP2, Ca-AMP1, Bm-AMP1, Ace-AMP1, Ac-AMP1, Ac-AMP2, Mj-AMP1, Mj-AMP2, Ib-AMP1, Ib-AMP2, Ib-AMP3, Ib-AMP4 and peptides derived therefrom or antifungal proteins showing 85% sequence similarity, preferably greater than 90% sequence similarity, more preferably greater than 95% sequence similarity, most preferably 96%, 97%, 98% or 99% sequence similarity with any of said proteins and are most particularly isolatable from edible varieties thereof.

In a particularly preferred embodiment of the invention the antifungal composition comprises one or more of the plant and seed derived antifungal proteins or peptides listed above, said antifungal proteins being particularly advantageous owing to their heat stability and stability to proteolytic degradation.

Particularly preferred compositions according to the invention and for use in the methods and uses of the invention comprise one or more of the antiftngal proteins Rs-AFP2, Rs-AFP1, Sa-AFPs, Bn-AFPs, Mj-AMP2, Ac-AMP1, Ib-AMP1 or Ib-AMP2 or derivatives thereof or antifungal proteins showing greater than 85% sequence similarity, preferably greater than 90% sequence similarity, more preferably greater than 95% sequence similarity and one or more of EDTA or a salt thereof, lactic acid, potassium sorbate,. sodium benzoate, propyl gallate, butylated hydroxy anisole, butylated hydroxytoluene or tertiary butyl hydroquinone.

The structure, isolation and purification of Rs-AFP2, Rs-AFP1, Bn-AFPs Sa-AFPs, Ib-AMP1, Ib-AMP2, Mj-AMP2 and Ac-AMP1 are described in Published International Patent Applications Nos. W093/05153, W095/24486, W092/15691 and W092/21699 respectively, the teaching of which is incorporated herein by reference.

As used herein the term derivatives denotes inter alia, peptides derived from the full length sequence such as those described in Published International Patent Application No. WO 97/21815 and also those where residues have been altered with respect to the native sequence such as those described in Published International Patent Application No. WO 97/21814.

In the context of the present invention, two amino acid sequences with at least 85% similarity to each other have at least 85% similar (identical or conservatively replaced) amino acid residues in a like position when aligned optimally allowing for up to 3 gaps, with the proviso that in respect of the gaps a total of not more than 15 amino acid residues is affected. Likewise, two amino acid sequences with at least 90% similarity to each other have at least 90% identical or conservatively replaced amino acid residues in a like position when aligned optimally allowing for up to 3 gaps with the proviso that in respect of the gaps a total of not more than 15 amino acid residues is affected.

For the purpose of the present invention, a conservative amino acid is defined as one which does not alter the activity/function of the protein when compared with the unmodified protein. In particular, conservative replacements may be made between amino acids within the following groups:

(i) Alanine, Serine, Glycine and Threonine
(ii) Glutamic acid and Aspartic acid
(iii) Arginine and Lysine
(iv) Isoleucine, Leucine, Valine and Methionine
(v) Phenylalanine, Tyrosine and Tryptophan Sequence similarity may. be calculated using methods well known in the art such as for example that described by Wilbur and Lipman (Proc. Natl. Acad. Sci. USA 80, 726–730 (1983)), Myers and Miller (Comput. Appl. Biosci. 4 11–17 (1988)) or Watterman and Eggert (J. Mol. Biol. (1987)197 723–28). The MegAlign Lipman-Pearson one pair method (using default parameters) which may be obtained from DNAstar Inc, 1228 Selfpark Street, Madison, Wis., 53715, USA as part of the Lasergene system may also be used.

Examples of other antifumgal agents include for example PR proteins such as chitinases, glucanases such as beta1,3 and beta1,6 glucanases, chitin-binding lectins, zeamatins, osmotins, thionins and ribosome-inactivating proteins. Examples of suitable chitinases and glucanases can be found for example, in Published European Patent Application EP 440304; of osmotin in Published International Patent Application No. WO 91/18984; of chitinase V in Published International Patent Application No. WO 95/05467; of chitin binding protein in Published International Patent Application No. WO 94/08009; beta1,6 glucanase in International Patent Application No. PCT/EP98102580.

The antifungal agents may be synthesised chemically or produced using recombinant DNA technology using methods well known in the art. Where the antifungal agent is produced using recombinant techniques in a microorganism host, the host used for the transformation and production of the desired agent will be a GRAS organism. GRAS organisms being those organisms such as, yeast, Pichia, lactic acid bacteria and certain *E. coli* strains which are regarded by the Regulatory Authorities as being 'safe'. Proteins thus produced using GRAS organisms may then be purified and added to foodstuffs in combination with food additives. The antifungal agents may also be used in the form of extracts such as seed or plant extracts where the extract contains the antifungal agent in partially purified or enriched form and the food additive is added to the extract. This is described more fully in the examples herein.

The methods and compositionsof the invention have been found to be . particularly effective against the common food-spoilage organisms *Fusarium culmorum, Penicillium chrysogenum, Penicillium roquefortii*, Alternaria sp., Cladosporium sp. *Trichoderma harzianum, Penicillium nalgiovense, Penicillium commune, Mucor plumbeus, Aspergillus versicolor* and *Scopulariopsis brevicaulis*. Samples of these organisms are available from for example The American Type Culture Collection (ATCC) in Rockville, Md., USA.

In a further aspect the invention provides a method of inhibiting fimgal growth in foodstuffs comprising exposing an environment in which said growth is to be inhibited to a fungicidally effective amount of an antifungal composition according to any of the above aspects of the invention.

In a yet further aspect the invention provides a method of inhibiting fungal growth in foodstuffs comprising applying to a foodstuff or to the locus of a foodstuff a fungicidally effective amount of an antifungal composition according to any of the above aspects of the invention.

The method and compositions of the invention are particularly suitable for use with a wide range of foods and beverages including fruits and jams and dairy products such as yoghurts, cheeses, cream desserts, milk shakes. The antiflngal compositions according to the invention are in a form suitable for use with foodstuffs for human and animal consumption. Other components of the composition may be chosen according to the nature of the foodstuff and to its method of consumption and this will be readily apparent to a man skilled in the art.

The environment in which it is desired to inhibit ftingal growth may be exposed to the composition comprising the antifiagal agent and the food additive in a variety of ways which will most usually be determined by the nature of the foodstuff to be protected. The foodstuff and the composition of the invention may, for example, be mixed together during the manufacturing process. Alternatively or additionally, the container in which the foodstuff is packaged may be sprayed with the composition before the foodstuff is added and/or sprayed with the composition after packing and/or filling. The composition of the invention may also be used in conjunction with coating products e.g. cheese wax.

In a further preferred embodiment the antifungal composition shows antifungal activity against one or more of *Fusarium culmorum, Penicillium chrysogenum, Penicillium roquefortii*, Alternaria sp., Cladbsporium sp., *Trichoderma harzianum, Penicillium nalgiovense, Penicillium commune, Mucor plumbeus, Aspergillus versicolor* and *Scopulariopsis brevicaulis*.

The antifungal proteins Rs-AFP2, Ib-AMP1, Ib-AMP2, Mj-AMP2, Bn-AFPs, Sa-AFPs and Ac-AMP1 have been tested as purified proteins and as seed-extracts in combination with different food additives against food spoilage fungal strains. Examples of food additives which we have identified as potentiating antifungal activity when combined with the antifungal proteins are listed in Table 1 which also. includes an indication of the maximum amounts currently allowed in different foodstuffs. The ratio of antifungal agent andthe food additive will generally be such that the level of food additive in the composition according to the invention will be significantly lower than the maximum concentration allowed. For example the food additive may be present in the composition at or between a level two to a hundred fold lower, more preferably four to fifty fold lower and most. preferably four to ten fold lower than the maximum concentration allowed for a particular foodstuff.

The antifungal agent and the food additive will generally be present in the compositions according to the invention and for use in the method of the invention in a respective ratio of from 1:0.5 to 1:900000, more preferably from 1:10 to 1:10000 and most preferably from 1:5 to 1:500.

TABLE 1

Maximum amounts allowed in foods of the additives shown to have a synergistic antifungal effect when combined with different AFPs.

| Food Additive | Max. Concentration Allowed | Examples of food categories |
|---|---|---|
| CaNa$_2$EDTA | 33 ppm | Soft drinks |
| | 25 ppm | Alcoholic drinks |
| | 200 ppm | Egg products |
| | 75 ppm | Mayonnaise, sauces |
| Na$_2$EDTA | 145 ppm | Canned peas |
| | 165 ppm | Canned beans |
| | 75 ppm | Dressings, mayonnaise |
| | 150 ppm | Aq. multivitamins |
| Na Benzoate | 1000 ppm | General |
| K Benzoate | 1000 ppm | Margarine, wine |
| Ca Benzoate | 1000 ppm | |
| Sorbic acid and its salts e.g. K and Na | 2000 ppm | Baked goods, beverages, cakes, cheese, fish, fruit juice, margarine, pickled goods, salad dressings, fresh salad, wine |
| Lactic acid | ADI no limit | beverages, cheese, wine, poultry, confectionery |

BRIEF DESCRIPTION OF THE DRAWINGS

The invention is further illustrated with reference to the following non-limiting examples and FIGS. in which:

FIG. 1. shows an Isobologram of the combination of Ib-AMP1 with Na$_2$H$_2$EDTA against *P. chrysogenum*

FIG. 2. shows an Isobologran of the combination of Ac-AMP1 with K sorbate against *P. roquefortii*

FIG. 3. shows an Isobologram of the combination of Rs-AFP2 with K sorbate against *P. roquefortii*

FIG. 4. shows an Isobologram of the combination of Ib-AMP1 with Na benzoate against *P. chrysogenum*

FIG. 5. shows an Isobologram of the combination of Ib-AMP1 with lactic acid against *P. chrysogenum*

FIG. 6. shows an Isobologram of the combination of Ib-AMP1 with BHIA against *P. chrysogenum*.

FIG. 7 shows the amino acid sequence for Rs-AFP1, Rs-AFP2, Dm-AMP1 and Dm-AMP2, Hs-AFP1, Ah-AMP1, Ct-AMP1, Bn-AFP1, Bn-AFP2, Br-AFP1, Br-A-FP2, Sa-AFP1, Sa-AFP2, Cb-AMP1, Cb-AMP2, Ca-AMP1, Bm-AMP1, Ace-AMP1, Ac-AMP1, Ac-AMP2, Mj-AMP1; Mj-AMP2, Ib-AMP1, Ib-AMP2, Ib-AMP3 and Ib-AMP4.

DETAILED DESCRIPTION OF THE INVENTION

Examples

Materials and Methods

Materials

Seeds of *Raphanus sativus; Amaranthus caudatus, Mirabilis jalapa* and *Impatiens balsamina* were obtained from Chiltern Seeds (Cumbria, UK). Seeds of *Brassica napus* and *Sinapis alba* were kindly donated by Cargill, Plc: Non-sterile flat-bottom 96-well microplates were used throughout the experiments. Na benzoate was kindly provided by Pfizer Ltd. K sorbate was obtained from Hoechst. EDTA and its Na and CaNa$_2$ salts were purchased from SIGMA.

Antifungal Assays

Routinely, tests were performed with 20 µl of test solution and 80 µl of a suspension of fungal spores (1×10$^4$ spores/ml) in Medium A (half strength potato dextrose broth or ½ PDB) or Medium B (½ PDB supplemented with 1 mM CaCl$_2$ and 50 mM KCl). Control microcultures contained 20 µl of sterile distilled water and 80 µl of the fungal spore suspension.

Unless otherwise stated the incubation was carried out at 24° C. for 48 hours. Percentages of fungal growth were estimated by microscopic examination of the microplates after the incubation period. The control microcultures were used as a reference in order to estimate fungal growth inhibition. The minimum concentration of protein or chemical compound required to give strong fungal growth inhibition, e. g. more than 90% fungal growth inhibition, was taken as the minimum inhibitory concentration (MIC) of the protein or compound considered.

Purification of Antifungal Proteins

The purification of the antiflugal proteins Ac-AMP1, Mj-AMP1, Rs-AFP2, Ib-AMP1 and Ib-AMP2 was performed as described by Broekaert, et al. (1992, Biochem., 31,4308–4314), Bruno et al. (1992, J. Biol. Chem., 267, 4, 2228–2233), Terras et al. (1992, J. Biol. Chem., 267, 22: 15301–15309) and by Broekart et al. (in Published International Patent application No. WO95/24486), respectively.

Results

Antifungal Potency of the Antifumgal Proteins

The antifungal potency of the purified proteins was assessed on different food spoilage fungi using the assay described above. Growth of fungi, collection and harvest of fungal spores were done as previously described (Broekaert et al., 1990, FEMS Microbiol. Lett., 69: 55–60).

The following fungal strains were used: *Fusarium culmorum, Penicillium chrysogenum, Penicillium roquefortii, Penicillium commune, Penicillium nalgiovense, Mucor plumbeus, Scopulariopsis brevicaulis, Aspergillus versicolor,* Alternaria sp., Cladosporium sp. and *Trichoderma harzianum.*

Serial dilutions of the antifungal proteins in double distilled water were applied to the fungal spore suspensions prepared in either growth medium A (half strength potato dextrose broth, ½ PDB) or medium B (medium A supplemented with 1 mM CaCl$_2$ and 50 mM KCl). The percentage growth inhibition was estimated by microscopic inspection of the microtitre plates, taking the microculture control with no antifungal protein added as a reference for normal fungal growth. The minimum concentration required to strongly inhibit fungal growth, e. g. more than 90% growth inhibition, after 48 hours of incubation (MIC value) was thus calculated.

The results obtained for Ib-AMP1 and Rs-AFP2 against a range of fungal strains in both media A and B are summarised in table 2. Both peptides show a broad spectrum of activity against the fungal strains tested. In the low-ionic strength (medium A) the MIC values are generally below 25 µg/ml. The activity of the peptides is sensitive to the ionic conditions used in the assay and in high salt medium (medium B) their activity is reduced.

TABLE 2

Comparison of the antifungal activities of Rs-AFP2 and Ib-AMP1 in low salt medium A (½ PDB) and in medium B (medium A containing 1 mM CaCl$_2$ and 50 mM KCl).

| FUNGUS | Ib-AMP1 (ppm) | Rs-AFP2 (ppm) |
|---|---|---|
| MEDIUM A | | |
| Alternaria sp. | 12.5 | 6.25 |
| Cladosporium sp. | 100 | 100 |
| F. culmorum | 6.25 | 3.1 |
| P. chrysogenum | 12.5 | >200 |
| P. roquefortii | 6.2 | 3 |
| T. harzianum | 25 | 200 |
| MEDIUM B | | |
| Alternaria sp. | 200 | 200 |
| Cladosporium sp. | >200 | >200 |
| F. culmorum | 100 | 12.5 |
| P. chrysogenum | >200 | >200 |
| P. roquefortii | 200 | 25 |
| T. harzianum | >200 | >200 |

Antifungal Potency of the Combination of Antifungal Proteins and Food Additives a) Antifungal Potency of the Antifungal Protein/EDTA Combination The food additive EDTA is used in foods as an antioxidant because of its role in chelating metal cations. No antifungal properties have been assigned to EDTA at the concentrations used in foods. However, the combination of an antifungal protein with EDTA in medium B resulted in an enhanced antifungal activity against the fungal strain tested, *Penicillium chrysogenum* and *Penicillium roquefortii*. Some of the results observed have been summarised in table 3 below. The potentiation of the activities of the antifungal proteins by EDTA and its salts in medium containing 1 mM CaCl$_2$ and 50 mM KCl are able to provide strong inhibition of fungal growth in vitro after 48 hours incubation at 24° C. with concentrations of both agents that are much lower than those required if they were used individually. In a similar way, the application of combinations of the antifungal proteins together with other additives to food preservation will allow a reduction in the amount of such additives added to the food.

TABLE 3

Concentrations reuired of the antifungal agents when used alone and in combination to give strong growth inhibition after 48 hours incubation at 24° C. in medium B (½PDB containing 1 mM CaCl$_2$ and 50 mM KCl).

| Fungal strain | Ib-AMP1 alone (ppm) | Na$_2$H$_2$EDTA alone (ppm) | Combination of Ib-AMP1 and Na$_2$H$_2$EDTA (ppm), (ppm) | Molar ratios Ib-AMP1: Na$_2$H$_2$EDTA |
|---|---|---|---|---|
| *Penicillium chrysogenum* | >200 | >150 | 6.25, 150 | 2.0 μM:400 μM 1:200 |
| | | | 12.5, 75 | 4.14 μM:200 μM 1:48 |
| | | | 100, 38 | 33.3 μM:100 μM 1:3 |

| Fungal strain | Ib-AMP1 alone (ppm) | CaNa$_2$EDTA alone (ppm) | Combination of Ib-AMP1 and CaNa$_2$EDTA (ppm), (ppm) | Molar ratios Ib-AMP1: CaNa$_2$EDTA |
|---|---|---|---|---|
| *Penicillium chrysogenum* | >200 | >150 | 25, 150 | 8.3 μM:400 μM 1:48 |
| | | | 100, 75 | 33.3 μM:200 μM 1:6 |
| *Penicillium roquefortii* | 200 | >150 | 25, 75 | 8.3 μM:200 μM 1:24 |
| | | | 50, 38 | 16.6 μM:100 μM 1:6 |
| | | | 100, 9 | 33.3 μM:25 μM 1:0.75 |

| Fungal strain | Ib-AMP1 alone (ppm) | EDTA alone (ppm) | Combination of Ib-AMP1 and EDTA (ppm), (ppm) | Molar ratios Ib-AMP1:EDTA |
|---|---|---|---|---|
| *Penicillium roquefortii* | 200 | >200 | 25, 100 | 8.8 μM:342 μM 1:40 |
| | | | 12.5, 200 | 4.4 μM:684 μM 1:160 |
| *Penicillium commune* | 100 | >200 | 25, 100 | 8.8 μM:342 μM 1:40 |
| | | | 12.5, 200 | 4.4 μM:684 μM 1:160 |

TABLE 3-continued

Concentrations reuired of the antifungal agents when used alone and in combination to give strong growth inhibition after 48 hours incubation at 24° C. in medium B (½PDB containing 1 mM CaCl₂ and 50 mM KCl).

| Penicillium chrysogenum | >200 | 200 | 25, 100 | 8.8 µM:342 µM 1:40 |

| Fungal strain | Rs-AFP2 alone (ppm) | EDTA alone (ppm) | Combination of Rs-AFP2 and EDTA (ppm), (ppm) | Molar ratios Rs-AFP2:EDTA |
| --- | --- | --- | --- | --- |
| Penicillium roquefortii | 25 | >200 | 6.25, 100 | 1.25 µM:342 µM 1:274 |
|  |  |  | 3.1, 200 | 0.625 µM:684 µM 1:1096 |
| Penicillium chrysogenum | >200 | 200 | 12.5, 100 | 2.50 µM:342 µM 1:137 | b) Antifungal Potency of the Combination of K Sorbate with Antifungal Proteins

Sorbic acid and its sodium, potassium and calcium salts are currently used in foodstuffs as preservatives, acting as mould retardants. The maximum amounts allowed in foods are shown in table 1. The combinations of sorbate with the antifungal proteins show an enhanced inhibition of fungal growth. Examples of some of the combinations that are capable of strongly inhibit fungal growth in the in vitro tests are shown on tables 4 and 5.

TABLE 4

Concentrations required of the antifungal proteins and K sorbate when used alone and in combination to give strong growth inhibition of the food spoilage strain *Penicillium chrysogenum* after 48 hours incubation at 24° C. in medium B (½PDB containing 1 mM CaCl₂ and 50 mM KCl).

| Antifungal protein | AFP alone (ppm) in medium B | K sorbate alone (ppm) | Combination of AFP and K sorbate (ppm), (ppm) | Molar ratios AFP:K sorbate |
| --- | --- | --- | --- | --- |
| Ac-AMP1 | >100 | 1000 | 50, 500 | 10 µM:3.3 mM 1:333 |
| Ib-AMP1 | >00 | 1000 | 25, 500 | 8.8 µM:3.3 mM 1:380 |
| Ib-AMP2 | >100 | 1000 | 25, 500 | 8.8 µM:3.3 mM 1:380 |
| Mj-AMP2 | >100 | 1000 | 25, 500 | 5 µM:3.3 mM 1:665 |
| Rs-AFP2 | >200 | 1000 | 6.2, 500 | 1.25 µM:3.3 mM 1:2662 |

TABLE 5

Concentrations required of the antifungal proteins and K sorbate when used alone and in combination to give strong growth inhibition of the food spoilage strain *Penicillium roquefortii* after 48 hours incubation at 24° C. in medium B (½PDB containing 1 mM CaCl₂ and 50 mM KCl).

| Antifungal protein | AFP alone (ppm) in medium B | K sorbate alone (ppm) | Combination of AFP and K sorbate (ppm), (ppm) | Molar ratios AFP:K sorbate |
| --- | --- | --- | --- | --- |
| Ac-AMP1 | >100 | 1500 | 25, 500 | 5 µM:3.3 mM 1:665 |
| Ib-AMP1 | 200 | 1500 | 100, 500 | 35.2 µM:3.3 mM 1:9 |
| Ib-AMP2 | 200 | 1500 | 50, 500 | 17.6 µM:3.3 mM 1:190 |
| Mj-AMP2 | 100 | 1500 | 25, 500 | 5 µM:3.3 mM 1:665 |
| Rs-AFP2 | 25 | 1500 | 3.1, 500 | 0.625 µM:3.3 mM 1:5,325 | c) Antifungal Potency of the Combination of Benzoic Acid and its Salts with Ib-AMP1 and Rs-AFP2

Benzoic acid and its Na and K salts are being used as a food preservative due to their antifungal activity, yeasts and moulds being more affected than bacteria. The maximum concentration permissible of benzoic acid and its salts in foods is 0.1%. Its presence may be readily perceptible in the flavour of the foods to which it is added.

The effect of Na benzoate on fungal growth when combined with the antifungal proteins Ib-AMP1 and Rs-AFP2 was tested on *Penicillium chrysogenum*. The results, summarised in tables 6 and 7, clearly show a synergistic antifungal effect that could be used for the application of the antifungal proteins to food preservation by helping to reduce the amount of Na benzoate required.

TABLE 6

Concentrations required of the antifungal agents Ib-AMP1 and Na benzoate when used alone and in combination to give strong growth inhibition after 48 hours incubation at 24° C. in medium B (½ PDB containing 1 mM $CaCl_2$ and 50 mM KCl).

| Fungal Strain | Ib-AMP1 alone (ppm) | Na benzoate (ppm) | Combination of Ib-AMP1 and benzoate | Molar Ratios Ib-AMP1:Na benzoate |
|---|---|---|---|---|
| Penicillium chrysogenum | >200 | 6000 | 100, 500 | 333 μM:3.5 mM 1:104 |

TABLE 7

Concentrations required of the antifungal agents Rs-AFP2 and Na benzoate when used alone and in combination to give strong growth inhibition after 48 hours incubation at 24° C. in medium B (½ PDB containing 1 mM $CaCl_2$ and 50 mM KCl).

| Fungal Strain | Rs-AFP2 alone (ppm) | Na benzoate (ppm) | Combination of Rs-AFP2 and benzoate (ppm), (ppm) | Molar Ratios Rs-AFP2:Na benzoate |
|---|---|---|---|---|
| Penicillium chrysogenum | >200 | 6000 | 200, 500 | 40 μM:3.5 mM 1:86.7 |
| Penicillium chrysogenum | >200 | 6000 | 6.25, 1000 | 1.25:6.9 mM 1:5,551 | d) Antiftingal Potency of the Combination of Lactic Acid with Ib-AMP1 on *Penicillium chrysogenum*.

Lactic acid is a food additive with different possible applications: acidulant, preservative, adjuvant, flavour enhancer or raising agent. It is considered as GRAS and has no ADI limit.

The effect of lactic acid on fungal growth when combined with the antifungal protein Ib-AMP1 was tested on *Penicillium chrysogenum*. The results, summarised in table 9, show a synergistic antifungal effect of the combination of the two agents.

TABLE 8

Concentrations required of the antifungal agents Ib-AMP1 and lactic acid when used alone and in combination to give strong growth inhibition after 48 hours incubation at 24° C. in medium B (½ PDB containing 1 mM $CaCl_2$ and 50 mM KCl).

| Fungal Strain | Ib-AMP1 alone (ppm) | Lactic acid (ppm) | Combination of Ib-AMP1 (ppm) and Lactic acid (ppm) | Molar Ratios Ib-AMP1:Lactic acid |
|---|---|---|---|---|
| Penicillium chrysogenum | >200 | 20,000 | 25, 10,000 200, 2,500 | 8.3 μM:111 mM 1:13400 |

TABLE 8-continued

Concentrations required of the antifungal agents Ib-AMP1 and lactic acid when used alone and in combination to give strong growth inhibition after 48 hours incubation at 24° C. in medium B (½ PDB containing 1 mM $CaCl_2$ and 50 mM KCl).

| Fungal Strain | Ib-AMP1 alone (ppm) | Lactic acid (ppm) | Combination of Ib-AMP1 (ppm) and Lactic acid (ppm) | Molar Ratios Ib-AMP1:Lactic acid |
|---|---|---|---|---|
| | | | | 66.6 μM:27.8 mM 1:417 | e) Antifungal Potency of Seed Extracts Combined with Food Additives

Seeds of radish (*Raphanus sativus*), oilseed rape (*Brassica napus*) and white mustard (*Sinapis alba*) were used to prepare extracts enriched in basic antifungal proteins that can be applied to the preservation of foods by combining them with currently used food additives, such as sorbate, sodium benzoate and EDTA. The basic protein containing extracts were prepared as published by Terras et al. (*J. Biol. Biochem.* (1992), 267, 22, 15301–15309). The antifungal activity of the extracts was assessed microscopically and expressed in units of activity, where 10 units represent the antifungal activity required to inhibit flngal growth in 1 ml of medium for 48 hours at 24° C.

As seen on the tables below, the antifungal activity of the extracts containing the basic protein fraction is dramatically reduced by the addition of 1 mM $CaCl_2$ and 50 mM KCl to the growth medium (half-strength potato dextrose broth). A significant proportion of the activity can be recovered if currently used food additives, such as EDTA, sodium benzoate and K sorbate, are added in combination with the extracts. The potentiation of the antifungal activity present in the extracts by the food additives makes it possible to use such combinations as part of preservation systems in a wide range of food products.

TABLE 10

Antifungal activity of the basic protein fractions obtained from edible seeds against *P. roquefortii*. Units of antifungal activity have been expressed per gram of seed. Enhancement of the antifungal activity of the extracts in medium B by the different food additives is clearly demonstrated. The concentrations of the additives K sorbate and Na benzoate are within the maximum allowed in foods. EDTA is an indirect food additive that is added as an antioxidant to the packaging materials. Similar potentiating effects by $Na_2H_2EDTA$ have also been observed.

| | | Extract | |
|---|---|---|---|
| Medium | Additive | Oilseed rape | White mustard |
| A | — | 32,000 | 2,000 |
| B | — | 250 | <250 |
| B | 75 ppm EDTA | 2,000 | 250 |
| B | 150 ppm EDTA | 4,000 | 1,000 |
| B | 400 ppm K sorbate | 1,000 | 250 |
| B | 750 ppm K sorbate | 16,600 | 4,000 |
| B | 400 ppm Na benzoate | 2,000 | <250 |
| B | 750 ppm Na benzoate | 4,000 | 250 |

TABLE 11

Potentation of the antifungal activity of the oilseed rape seed basic protein extract by K sorbate against food spoilage Penicillium spp. Units of antifungal activity have been expressed per gram of seed.

| Fungal strain | Activity in medium B | Activity in medium B + 400 ppm K sorbate | Activity in medium B + 750 ppm K sorbate |
|---|---|---|---|
| Penicillium commune | 0 | 2,000 | 4,000 |
| Penicillium nalgiovense | 0 | 4,000 | 8,000 |
| Penicillium chrysogenum | 0 | 0 | 1,000 |

TABLE 12

Potentation of the antifungal activity of the oilseed rape basic protein extract by Na benzoate against fungal food spoilage strains. Units of antifungal activity have been expressed per gram of seed.

| Fungal strain | Activity in medium B | Activity in medium B + 400 ppm Na benzoate | Activity in medium B + 750 ppm Na benzoate |
|---|---|---|---|
| Aspergillus versicolor | <250 | 16,000 | 32,000 |
| Scopulariopsis brevicaulis | 2,000 | 8,000 | 16,000 |

TABLE 13

Potentation of the antifungal activity of the radish seed basic protein extract by K sorbate against Penicillium roquefortii. Units of antifungal activity have been expressed per gram of seed.

| Seed extract | Activity in medium A | Activity in medium B | Activity in medium B + 400 ppm K sorbate | Activity in medium B + 750 ppm K sorbate |
|---|---|---|---|---|
| Radish | 45,000 | 2,240 | 10,000 | 80,000 | f) Antifungal Potency of the Combination of Phenolic Antioxidants and Ib-AMP 1

Phenolic antioxidants include butytlated hydroxyanisole (BHA), butylated hydroxytoluene (BHT), tertiary butylhydroquinone (TBHQ) and propyl gallate (PG). These compounds are added to foods to prevent the autoxidation of unsaturated lipids. In the United States and at least 60 other countries they are GRAS for use in foods as antioxidants at a maximum concentration of 200 ppm of oil or fat content (Davidson, P. M. (1993) Parabens and phenolic compounds. In: Antimicrobials in foods. Edited by P. M. Davidson and A. L. Branen. Marcel Dekker, Inc. New York). At this maximum concentration allowed in foods they do not act as food preservatives, although they show antibacterial and antifungal activities at higher concentrations.

The antifungal activity of low concentrations of BHA used in combination with the antifungal protein Ib-AMP1 was studied in vitro against a range of food spoilage strains.

BHA was dissolved in 50% ethanol and added to the growth medium (half-strength potato dextrose broth containing 1 mM $CaCl_2$ and 50 mM KCl) to give the required final concentrations (200, 100, 50 and 25 ppm). The Ib-AMP1 pure protein was added to the test solution and mixed with the fungal spore suspension as described above. Following inoculation the plates were incubated at 24° C. for 48 hours. Fungal growth inhibition was assessed microscopically by comparison with controls which did not contain neither BHA nor Ib-AMP1. A summary of the results obtained is shown on table 14.

TABLE 14

Minimum inhibitory concentration of the antifungal protein Ib-AMP1 and the phenolic antioxidant BHA capable of strong inhibition of fungal growth when used alone and in combination in medium B, after 48 hours incubation at 24° C.

| Strain | Ib-AMP1 alone (ppm) | BHA alone (ppm) | Combination Ib-AMP1 + BHA (ppm), (ppm) | Molar ratios Ib-AMP1:BHA |
|---|---|---|---|---|
| Mucor plumbeus | >200 | >200 | 1.5, 200 | 0.5 $\mu$M:1.1 mM 1:2,218 |
| Alternaria sp. | 200 | >200 | 1.5, 100 | 0.5 $\mu$M:555 $\mu$M 1:1,110 |
| Cladosporium sp. | >200 | >200 | 100, 100 | 33.3 $\mu$M:555 $\mu$M 1:17 |
| P. roquefortii | 200 | >200 | 25, 50 | 8.3 $\mu$M:277 $\mu$M 1:33 |
| P. chrysogenum | >200 | >200 | 25, 50 | 8.3 $\mu$M:277 $\mu$M 1:33 |
| Trichoderma harzianum | >200 | >200 | 25, 50 | 8.3 $\mu$M:277 $\mu$M 1:33 |
| Fusarium culmorum | 100 | >200 | 25, 100 | 8.3 $\mu$M:555 $\mu$M 1:66 |

Thus, a clear potentiation of the antifungal activity of the antiflugal protein Ib-AMP1 by low concentrations of BHA was determined. At the maximum concentration of BHA tested (200 ppm) no antifungal activity was observed if BHA was added alone to the growth medium. In a similar way, addition of 100 or 200 ppm Ib-AMP1 to the growth medium was sufficient to strongly inhibit growth of several of the flugal strains tested, but not all of them. The combined application of BHA and Ib-AMP1 was, however, able to strongly inhibit the growth of all the strains tested. Such observation makes it possible to try to preserve foods by combining an antifungal protein containing extract with a GRAS phenolic antioxidant, without exceeding the maximum allowed concentration of the antioxidant present in the food.

g) Antifungal Potency of the Combination of K Sorbate with Chitinase-I and Glucanase-I The enzymes chitinase-I and $\beta$-1,3-glucanase are capable of degrading fungal cell walls of growing hyphae when they are used in combination, ideally in a 1:1 ratio. This observation explains the role of these proteins in the plant defence mechanism against fungal pathogens. Inhibition of spore germination, however, seems to be relatively unaffected by the presence of these enzymes. Furthermore, it has been observed that fungal hyphae are able to become resistant when germinated in the presence of chitinase-I and $\beta$-1,3-glucanase.

These observations hinder the application of extracts containing the enzymes chitinase-I and $\beta$-1,3-glucanase to food preservation, where inhibition of spore germination is of paramount importance.

It is in this context that the possible combined application of Chi/Glu with food additives to try to prevent flngal spoilage of foods was considered. Chitinase-I and $\beta$-1,3-glucanase were extracted and purified from tobacco according to the method published by Sela-Buurlage, M. B., et al., in 1993 (Plant Physiol. 101, 857–863). The purified enzymes were mixed in a 1:1 ratio and then tested for antifungal activity against the food spoilage fungal strains Penicillium roquefortii and P. chrysogenum. The antifungal assays were carried out as described above. Assessment of growth inhibition was carried out by microscopic examination after 48 and 96 hours incubation at 24° C.

As seen on the table below, a clear synergistic potentiation of the antifungal activity of the enzymes by the food additive K sorbate was observed. The synergism was clearly shown after 96 hours incubation, as K sorbate alone was clearly unable to delay fungal growth for longer than 48 hours. In fact fungal growth inhibition by K sorbate was estimated to be of only 10–20% of the controls after 96 hours incubation. Fungal growth in the presence of up to 100 ppm of each of the enzymes chitinase-I and β-1,3-glucanase was equivalent to growth of the control, i.e. no inhibition was observed. Thus, the effect of the combined application of the antifungal agents was expected to be the same of the application of K sorbate on its own. Surprisingly, strong growth inhibition, i.e. growth inhibition higher than 90% as compared to control, was detected.

TABLE 15

Concentrations required of the proteins chitinase-I and glucanase-I and K sorbate when used alone and in combination to give strong growth inhibition of the food spoilage strains *Penicillium roquefortii* and *P. chrysogenum* after 96 hours incubation at 24° C. in medium B (½ PDB containing 1 mM CaCl$_2$ and 50 mM KCl).

| Fungal Strain | Chi-I/Glu-I (ppm) | K sorbate alone (ppm) | Combination of Chi-I/Glu-I and K sorbate (ppm), (ppm) |
|---|---|---|---|
| *Penicillium roquefortii* | >100 | >2,000 | 3.1, 2,000 |
| *Penicillium chrysogenum* | >100 | >2,000 | 6.25, 2,000 |

In all the examples included above, strong inhibition of fungal growth, equivalent to more than 90% growth inhibition, has been obtained by combining sub-inhibitory concentrations of each of the compounds when used alone. In order to assess the nature of the interaction between two agents, whether it is an additive, synergistic or antagonistic io interaction a mathematical expression described by Colby can be used (Colby, S. R. (1967) Calculating synergistic and antagonistic responses of herbicide combinations. Weeds 15, 20–22).

In Colby's formula, $E_1=X_1Y_1/100$, $X_1$ and $Y_1$ represent growth as a percentage of control with compound A (dosage p) and compound B (dosage q), respectively. $E_1$ is the i5 expected growth as a percentage of control with the mixture A and B (dosage p+q). The observed response ($E_{obs}$), expressed as percent inhibition of control, is obtained by combining the two compounds at dosages p and q, respectively. Comparison of the observed and expected percent inhibition responses ($E_{obs}/E_{exp}$) indicates synergism ($E_{obs}/E_{exp}>1$) or antagonism ($E_{obs}/E_{exp}<1$).

Colby's equation has been applied to several examples taken from the tables shown above, in order to demonstrate that synergistic effects have been observed. The application of Colby's equation to some of the combinations reported are reported below, to serve as an example on how the synergistic interaction was identified.

In the experiments described, where antifungal activity is measured using dilution tests, the presence of a synergistic effect may also be determined using isobolograms (Parish M. E. and Davidson P. M. (1993) Methods for evaluation. In: Antimicrobials in foods. Ed. By P. M. Davidson and A. L. Branen. Marcel Dekker, Inc. New York). Isobolograms are graphical representations of the minimum inhibitory concentrations (MIC) of two different antifungal agents required to strongly inhibit growth of a fungus. The concentrations of the two antifungal agents are arranged in each axis from lowest to highest concentration. If the concentrations that strongly inhibit growth fall on an approximately straight line that connects the individual MIC values on each axis the combined effect is additive. Deviation of the linearity to the left of the additive line will mean synergism. Isobolograms for some of the combinations are included in the examples given below, in order to confirm the results obtained by applying Colby's formula.

a) Combination of 12.5 ppm Ib-AMP1 with 75 ppm Na$_2$H$_2$EDTA

The individual application of 12.5 ppm Ib-AMP1 to a spore suspension of *Penicillium chrysogenum* in medium B resulted in 100% fungal growth, as compared to the control. On the other hand, application of 75 ppm Na$_2$H$_2$EDTA resulted in 90% growth of *P. chrysogenum*. According to Colby's equation, the expected growth would be $E_1=100*90/100=90\%$. However, the observed growth of *P. chrysogenum* in the presence of 12.5 ppm Ib-AMP1 and 75 ppm Na$_2$H$_2$EDTA was estimated to be of only 5% of the control. Thus, the ratio between the observed and the expected responses is $E_{obs}/E_{exp}=95/10=9.5$, which clearly indicates a synergistic interaction between Ib-AMP1 and Na$_2$H$_2$EDTA.

b) Combination of 25 ppm Ac-AMP1 with 500 ppm K Sorbate Against *P. roquefortii*

The individual application of 25 ppm Ac-AMP1 to a spore suspension of *Penicillium roquefortii* in medium B resulted in 100% fungal growth, as compared to the control. The application of 500 ppm K sorbate on its own resulted in 90% growth of *P. roquefortii*. According to Colby's equation, the expected growth would be $E_1=100*90/100=90\%$. However, the observed growth of *P. roquefortii* in the presence of 25 ppm Ac-AMP1 and 500 ppm K sorbate was estimated to be of only 5% of the control, Thus, the ratio between the observed and the expected responses is $E_{obs}/E_{exp}=95/10=9.5$, which clearly indicates a synergistic interaction between Ac-AMP1 and K sorbate.

c) Combination of 3.1 ppm Rs-AFP2 with 500 ppm K sorbate Against *P. roquefortii*

The individual application of 3.1 ppm Rs-AFP2 to a spore suspension of *Penicillium roquefortii* in medium B resulted in 100% fungal growth, as compared to the control. The application of 500 ppm K sorbate on its own resulted in 90% growth of *P. roquefortii*.

According to Colby's equation, the expected growth would be $E_1=100*90/100=90\%$. However, the observed growth of *P. roquefortii in the presence of* 3.1 ppm Rs-AFP2 and 500 ppm K sorbate was estimated to be of only 5% of the control. Thus, the ratio between the observed and the expected responses is $E_{obs}/E_{exp}=95/10=9.5$, which clearly indicates a synergistic interaction between Rs-AFP2 and K sorbate.

d) Combination of 100 ppm Ib-AMP1 with 500 ppm Na Benzoate Against *P. chrysogenum*

The individual application of 100 ppm Ib-AMP1 to a spore suspension of *Penicillium chrysogenum* in medium B resulted in 100% fungal growth, as compared to the control. On the other hand, application of 500 ppm Na benzoate resulted in an estimated 99% growth of *P. chrysogenum*. According to Colby's equation, the expected growth would be $E_1=100*99/100=99\%$. However, the observed growth of *P. chrysogenum* in the presence of 100 ppm Ib-AMP1 and 500 ppm Na benzoate was estimated to be of only 5% of the control. Thus, the ratio between the observed and the expected responses is $E_{obs}/E_{exp}=95/1=95$, which clearly indicates a synergistic interaction between Ib-AMP1 and Na benzoate.

e) Combination of 200 ppm Ib-AMP1 with 2500 ppm Lactic Acid Against *P. chrysogenum*

The individual application of 200 ppm Ib-AMP1 to a spore suspension of *Penicillium chrysogenum* in medium B resulted in 100% fungal growth, as compared to the control. On the other hand, application of 2500 ppm lactic acid resulted in an estimated 90% growth of *P. chrysogenum*. According to Colby's equation, the expected growth would be $E_1=100*90/100=90\%$. However, the observed growth of *P. chrysogenum* in the presence of 200 ppm Ib-AMP1 and 2500 ppm lactic acid was estimated to be of only 5% of the control. Thus, the ratio between the observed and the expected responses is $E_{obs}/E_{exp}=95/10=9.5$, which clearly indicates a synergistic interaction between Ib-AMP1 and lactic acid.

f) Combination of Ib-AMP1 and BHA

The individual application of 25 ppm Ib-AMP1 to a spore suspension of *Penicillium chrysogenum* in medium B resulted in 100% fungal growth, as compared to the control. On the other hand, application of 50 ppm BHA resulted in 99% growth of *P. chrysogenum*. According to Colby's equation, the expected growth-would be $E_1=100*99/100=99\%$. However, the observed growth of *P. chrysogenum* in the presence of 25 ppm Ib-AMP1 and 50 ppm BHA was estimated to be of only 5% of the control. Thus, the ratio between the observed and the expected responses is $E_{obs}/E_{exp}=95/1=95$, which clearly indicates a synergistic interaction between Ib-AMP1 and lactic acid.

What is claimed is:

1. An antifungal composition comprising one or more antifungal agents and one or more food additives wherein said one or more antifungal agents is an antifungal protein which is isolated from or is present in an extract of a seed of a plant of the genera selected from the group consisting of Raphanus, Brassica, Sinapis, Amaranthus, Impatiens, and Mirabilis, and said one or more food additives is selected from the group consisting an acid, a salt of said acid, an ester of said acid and a C1–6 alkyl ether, and wherein said one or more antifungal agent(s) and said one or more food additive(s) produce a synergistic effect on the overall antifungal activity of the composition in comparison to the antifungal activity of the antifungal agent alone, and are present in the composition in a respective ratio of from 1:0.5 to 1:900000; provided that said composition does not contain nisin, lactoferrin and derivatives thereof, trichorzianine or lysozyme.

2. A method of producing a synergistic enhancement in the antifungal properties of an antifungal agent comprising preparing a composition comprising one or more antifungal agents as defined in claim 1 and one or more food additives as defined in claim 1, wherein said one or more antifungal agent(s) and said one or more food additive(s) are present in the composition in a respective ratio of from 1:0.5 to 1:900000 and produce a synergistic effect on the overall antifungal activity of the composition in comparison to the antifungal activity of the antifungal agent alone.

3. An antifungal composition according to claim 1 wherein the food additive is selected from the group consisting of ethylenediaminetetraacetic acid, sorbic acid, benzoic acid, lactic acid, a lactic acid salt, a lactic acid ester, propyl gallate, butylated hydroxyanisole, butylated hydroxytoluene and tertiary-butyl hydrdquinone.

4. An antifungal composition according to claim 1 wherein the antifungal agent is heat stable.

5. An antifungal composition according to claim 4 wherein the antifungal agent is isolated from a seed thereof.

6. An antifungal composition according to claim 5 wherein the antifungal agent is isolated from an edible seed thereof.

7. An antifungal composition according to claim 1 comprising one or more antifungal proteins selected from the group consisting of Rs-AFP2, Rs-AFP1, Sa-AFPs, Bn-AFPs, Mj-AMP2, Ac-AMP1, Ib-AMP1, Ib-AMP2 and antifungal proteins showing greater than 85% amino acid sequence similarity to any of Rs-AFP2, Rs-AFP1, Sa-AFPs, Bn-AFPs, Mj-AMP2, Ac-AMP1, Ib-AMP1, and Ib-AMP2.

8. An antifungal composition according to claim 1 wherein the antifungal agent is present in a seed extract.

9. A method of inhibiting fungal growth in foodstuffs comprising exposing the environment of said foodstuffs to a fungicidally effective amount of an antifungal composition according to claim 1.

10. A method of inhibiting fungal growth in foodstuffs comprising applying to a foodstuff or the locus of a foodstuff a fungicidally effective amount of an antifungal composition according to claim 1.

11. The method of claim 2 wherein said one or more food additive are selected from the group consisting of ethylenediaminetetraacetic acid, sorbic acid, lactic acid, benzoic acid, a benzoic acid salt, a benzoic acid ester, propyl gallate, butylated hydroxyanisole, butylated hydroxytoluene and tertiary-butyl hydroquinone.

12. The method of claim 2 wherein said one or more antifungal agents are isolated from an edible seed.

* * * * *